(12) United States Patent
Erman et al.

(10) Patent No.: US 6,423,874 B1
(45) Date of Patent: Jul. 23, 2002

(54) PROCESS FOR OBTAINING FRAGRANT KETONE

(75) Inventors: Mark B. Erman, Atlantic Beach; Melissa J. Williams; Carlos G. Cárdenas, both of Jacksonville, all of FL (US)

(73) Assignee: Millennium Speciality Chemicals, Inc., Jacksonville, FL (US)

( * ) Notice: Subject to any disclaimer, the term of this patent is extended or adjusted under 35 U.S.C. 154(b) by 0 days.

(21) Appl. No.: 09/506,984

(22) Filed: Feb. 18, 2000

(51) Int. Cl.$^7$ ............................ C07C 45/67; C07C 69/74
(52) U.S. Cl. ..................... 568/341; 568/350; 568/352; 568/367; 568/374; 560/126
(58) Field of Search ................................ 568/374, 341, 568/350, 352, 367; 560/126, 128

(56) References Cited

U.S. PATENT DOCUMENTS

| 4,777,322 A | * 10/1988 | Hoelderich et al. |
| 5,180,709 A | 1/1993 | Etzweiler et al. |
| 5,214,160 A | 5/1993 | Etzweiler et al. |

FOREIGN PATENT DOCUMENTS

| DE | 519 450 | 2/1972 |
| EP | 0 464 357 | 1/1994 |
| EP | 0743297 A1 | 11/1996 |
| EP | 0957075 | 4/1999 |
| EP | 0985651 A1 | 3/2000 |
| JP | 11349518 A | 5/1999 |

OTHER PUBLICATIONS

Frater, et al., "Fragrance Chemistry," Tetrahedron, 54, 7633–7703 (1998).
Larock, "Comprehensive Organic Transformations, A Guide to Functional Group Preparations," pp. 110–114.
Nussbaumer, et al., "(±–1–[1R*,2R*, 8aS*)–1,2,3,5,6,7,8, 8a–Octahydro–1,2,8,8–tetramethylnaphthalen–2yl] ethan–1–one: Isolation and Stereoselective Synthesis of a Powerful Minor Constituent of the Perfumery Synthetic Iso E Super®," Helvetica Chimica Acta, vol. 82, pp. 1016–1024 (1999).
Cornelius Nussbaumer, Georg Frater and Philip Kraft, "Isolation and Stereoselective Synthesis of a Powerful Minor Constituent of the Perfumery Synthetic Iso E Super®," Helvetical Chmica Acta—vol. 82 (1999).
CA 132:22227x Zhixi Huan, et al., "Synthesis of Nut Type Perfume 5—methyl–2–Hepten–4–One," Faming Zhuanli Shenquing Gongkai Shuomingshu CN 1,198,432 (CL. C07C49/203), Nov. 11, 1998, Appl. 97,106,408, May 5, 1997; 7pp. (Ch).

* cited by examiner

Primary Examiner—Johann Richter
Assistant Examiner—Sikarl A. Witherspoon
(74) Attorney, Agent, or Firm—Needle & Rosenberg, P.C.

(57) ABSTRACT

A process for obtaining Ketone of formula 1a,b, which includes contacting a Ketone represented by formula 2a,b with a first catalyst under conditions and for a time sufficient to obtain an intermediate mixture, which intermediate mixture contains a Ketone represented by formula 4a,b; and contacting the intermediate mixture, or a fraction thereof, with a second catalyst under conditions effective to provide a product containing a Ketone of formula 1a,b. Moreover, the first catalyst preferably differs from the second catalyst with the first catalyst preferably being an isomerization catalyst and the second catalyst being a cyclization catalyst. The process is capable of providing unexpectedly increasased yields of both Ketone 4 and Ketone 1.

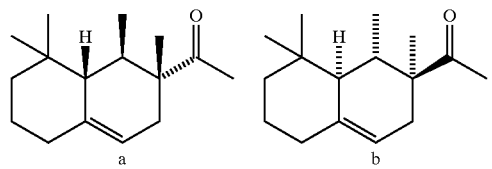

Formula 1

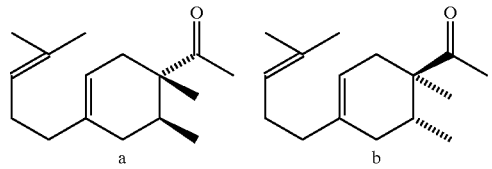

Formula 2

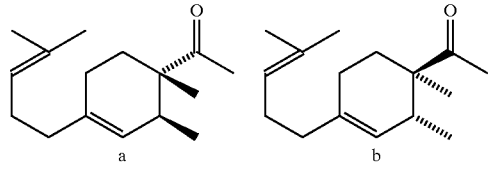

Formula 4

27 Claims, No Drawings

PROCESS FOR OBTAINING FRAGRANT KETONE

FIELD OF THE INVENTION

The invention relates to methods for obtaining compounds useful in perfumery, particularly to methods for obtaining ketones such as that having formula 1a,b (3α-acetyl-2,3,4α,4aβ,5,6,7,8-octahydro-3β,4β,5,5-tetramethylnaphthalene) in its racemic or optically active form:

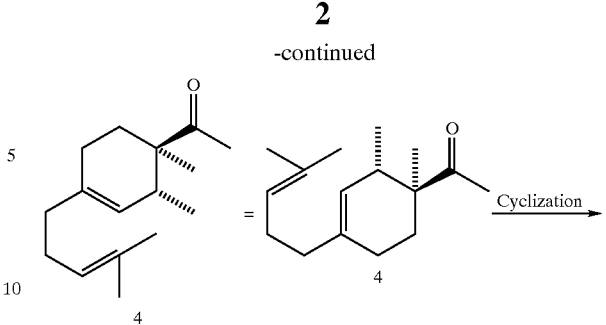

Formula 1

For simplicity, only one enantiomer will be shown for ketone 1 and its precursors in the following text and schemes of this Application, although the invention may relate to either enantiomeric mixtures or optically pure materials.

BACKGROUND OF THE INVENTION

Ketones according to Formula 1 are recognized in the art.

For example, G. Fráter et al. (Tetrahedron, 1998, Vol. 54, pp. 7633–7703, especially pp. 7651–7653) and C. Nussbaumer et al. (Helvetica Chimica Acta, 1999, Vol. 82, pp.1016–1024) discuss ketone 1 as an impurity in a commercial product Iso E Super®, which is obtained by an acid catalyzed cyclization of ketone 2 (Scheme 1) and which contains mainly ketone 3.

Despite its small concentration in Iso E Super®, ketone 1 is apparently responsible for the intense amber-woody odor of the whole product. This is because ketone 1 has an extremely low odor threshold of about 5 pg/L. The formation of ketone 1 during the cyclization of 2 can be explained via partial isomerization of starting material 2 into ketone 4 followed by the cyclization of the latter. However, the small concentration of ketone 1 in the product is believed to be due to a higher rate of the cyclization of 2 into 3 compared to the rate of its isomerization into 4.

Scheme 1

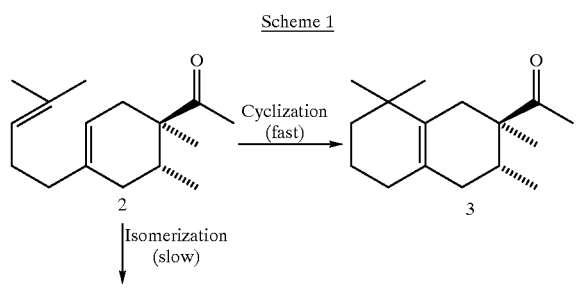

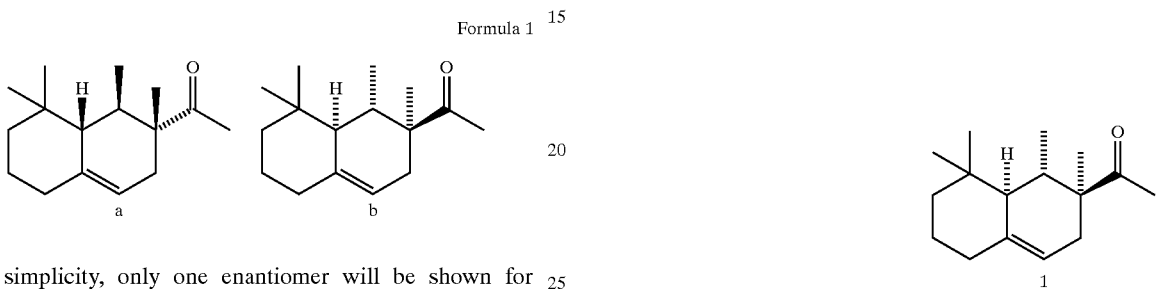

Copending U.S. patent application Ser. No. 09/136,488 (M. Erman et al., Millennium Specialty Chemicals, Inc.) shows that the concentration of ketone 1 in the product of cyclization of 2 can be increased when the reaction is carried out in the presence of hydroxyl-containing compounds. While the positive effect on yield by way of this process is significant, the concentration of ketone 1 remains less than about 10%.

Alternatively, a sophisticated multi-step synthesis of ketone 1 from α-ionone according to the Scheme 4 below was disclosed in EP 464357, U.S. Pat. Nos. 5,180,709, and 5,214,160 (F. Etzweller et al., Givaudan-Roure S.A.), and also in: C. Nussbaumer et al. (Helv.Chim. Acta, 1999, Vol. 82, pp.1016–1024). The method comprises a cuprate methylation of α-ionone into ketone 10, haloform oxidation to acid 11, conversion into ester 12, hypochlorite oxidation to allylic chloride 13, ozonolysis and subsequent Zn reduction to ketone 14, addition of acetylene followed by partial hydrogenation of the resulting lactone 15, methylation and silylation of lactone 16 to give enol silyl ether 17, its thermal rearrangement into ketone 18, and finally methylation with MeLi providing ketone 1. Multiplication of yields given in Scheme 4 shows that the total yield of ketone 1 based on α-ionone is below 8% of the theory.

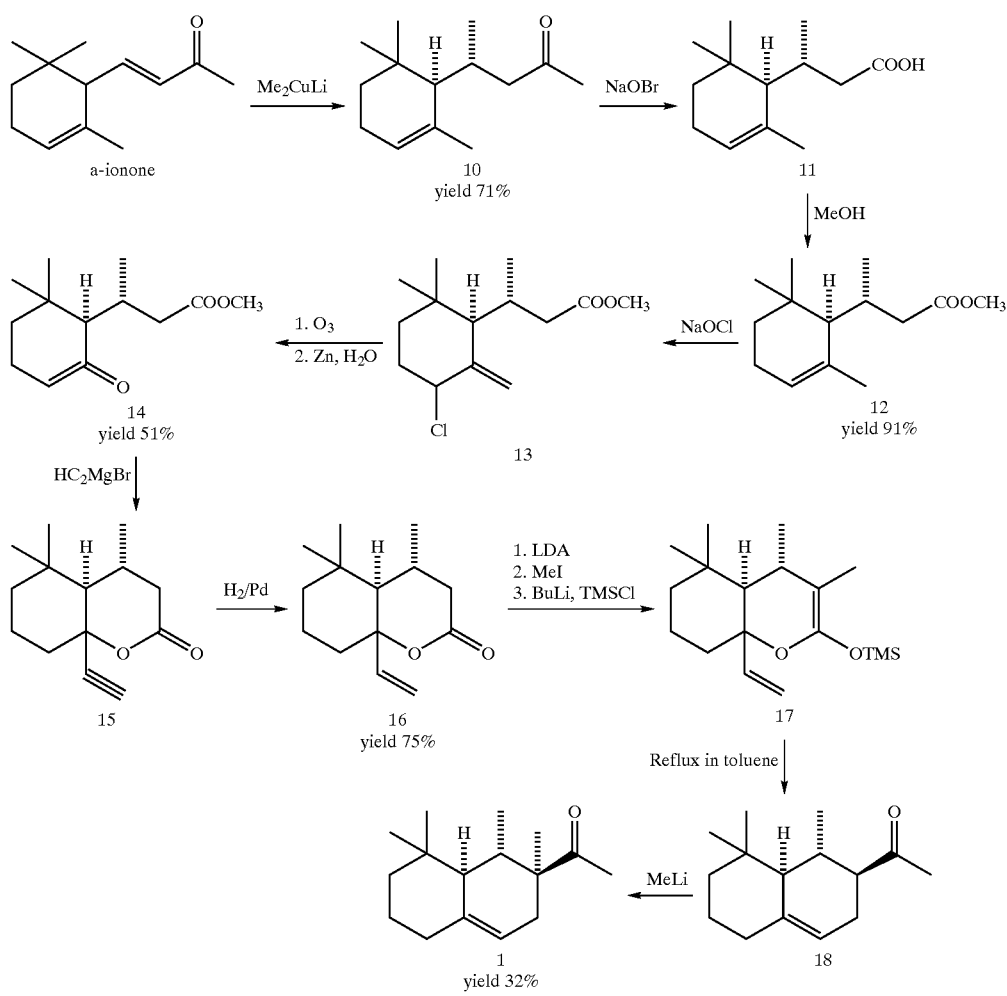

Scheme 2

Furthermore, the complexity of this synthesis severely limits its commercial applicability.

Thus, there are basically two known techniques for the preparation of ketone 1:
1) A multi-step synthesis from (α-ionone; and
2) A one-step synthesis from ketone 2, which provides isomeric mixtures containing ketone 1.

Both techniques, however, provide a yield of ketone 1 that is typically less than 10%. Unfortunately, isolation of ketone 1 from mixtures containing less than 10% ketone 1 concentration is a laborious and a low-yield process. Thus, the need still exists for an improved process for making ketone 1.

SUMMARY OF THE INVENTION

The present invention is based, at least in part, on the surprising discovery that contacting a ketone 2 with certain catalytic materials can cause its isomerization into ketone 4, thus providing, in high yield, intermediate mixtures containing ketone 4 and unreacted ketone 2, together with smaller amounts of other ketones, e.g., ketones 19 and 20 with a terminal double bond, and also smaller amounts of other cyclization products, ketones 1, 3, 7, 8, 9. Moreover, it has been discovered that the desirable isomerization of ketone 2 into ketones 4 and 19 can be significantly faster than the cyclization of ketone 2 into ketones 3, 7, and 8, and also faster than the secondary cyclization of 4 into 1 and 9. After a separate step of the cyclization of the intermediate mixture, a significant improvement in the yields of ketone 1 can be obtained.

In one aspect, the present invention relates to a process for obtaining ketone 1 that includes the steps of:
  a. isomerization of ketone 2 into a mixture of isomeric ketones including ketone 4;
  b. cyclization of the mixture of isomeric ketones into a mixture containing ketone 1, where the amount of ketone 1 is increased as compared to existing techniques. The process can further include an optional purification of ketone 1.

Each of steps a and b preferably employ a catalyst, and the catalyst for step a differs from that of step b.

The present invention will be discussed in greater detail below.

DETAILED DESCRIPTION OF THE PREFERRED EMBODIMENTS OF THE INVENTION

One embodiment of the invention process is schematically illustrated below.

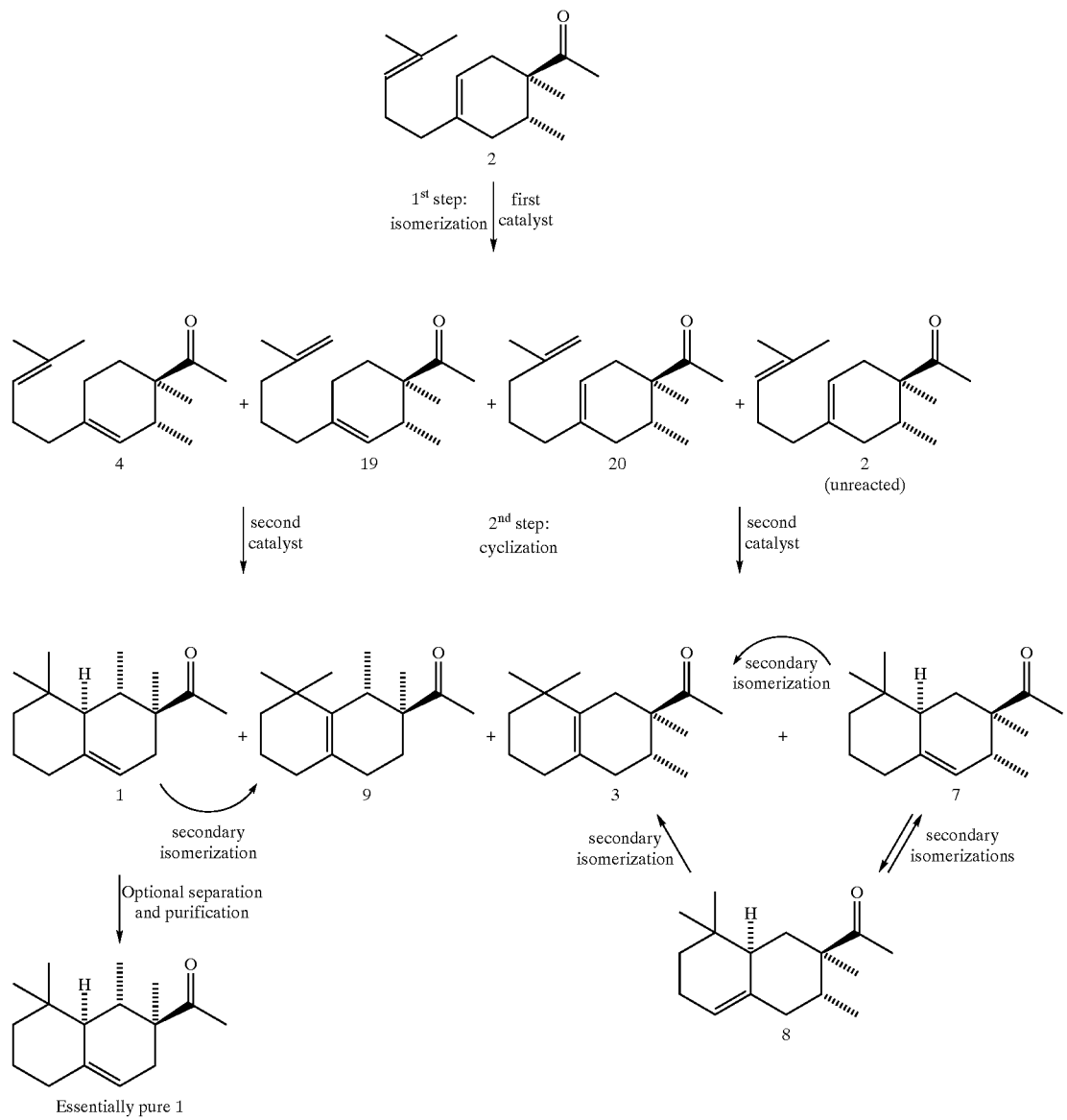

Scheme 3
Synthesis of ketone 1 according to the invention

Thus, in one preferred embodiment, the invention provides a process for obtaining ketone of formula 1a,b in its racemic or optically active form, comprising:

a. contacting a ketone represented by formula 2a,b in its optically active or racemic form with an isomerization catalyst under conditions and for a time sufficient to obtain an intermediate mixture, which intermediate mixture contains a ketone represented by formula 4a,b in its optically active or racemic form; and b. subsequently contacting the intermediate mixture, or a fraction thereof, with an acid catalyst.

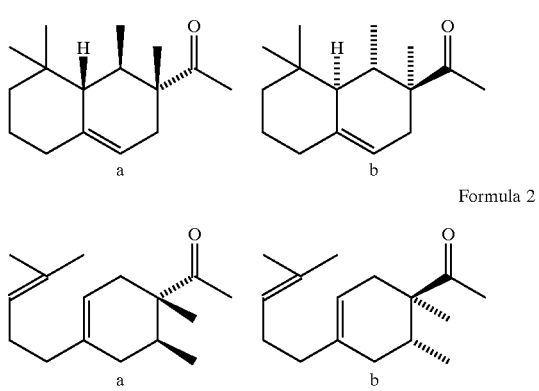

-continued

Formula 4

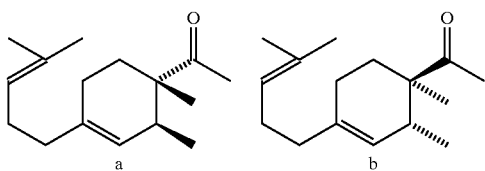

"Ketone of formula 1a,b in its racemic or optically active form," refers to ketone of formula 1a, ketone of formula 1b, or a mixture of ketones 1a and 1b in a racemic or optically active ratio. The ketone 2a,b is preferably present in a starting material also containing its structural isomers. To this end, the ketone 2a,b is preferably the main component in the starting material and is preferably present in an amount of about 70% to about 99% by weight of the starting material.

The process of the present invention allows for the production of significant amounts of ketone 4a,b. By "significant" it is meant an amount greater than a trace or impurity level of the component.

The molar conversion of ketone 2a,b to ketone 4a,b in step (a) is preferably greater than about 5%, more preferably 11%, and even more preferably greater than about 20%, specifically about 20% to about 30%. The intermediate mixture further contains unreacted ketone 2, preferably present in an amount greater than 20%, more preferably greater than 30% specifically about 30% to about 60%. The intermediate mixture may further comprise ketones with a terminal double bond, such as those represented by formulas 20a,b and/or 19a,b.

Formula 20

Formula 19

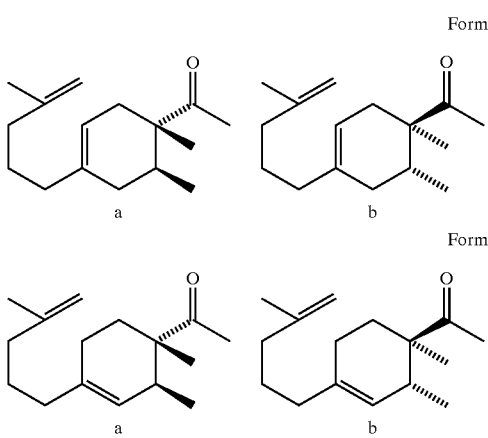

Accordingly, in one particularly preferred embodiment, the ketone 4a,b is one of three major constituents of the intermediate mixture.

The term "mainly" refers to a composition in which the "main" constituent is present in a larger proportion than the other constituent(s).

The term "major" similarly refers to components that are greater in proportion to the overall mixture than any other components. Thus, if a component is one of three major components, the component is the first, second, or third highest concentration component of all components in the composition.

This step employs a catalyst suitable for forming ketone 4a,b, which catalyst is preferably an isomerization catalyst. The isomerization catalysts can include any catalysts recognized in the art that are suitable for catalyzing an isomerization reaction. Examples of suitable materials include various classes and groups of compounds such as salts, oxides, hydroxides, acids, heteropolyacids, complexes, metals, metal hydrides, amides, metal-graphite intercalation compounds, transition metals on carriers, clays, sorbents, zeolites, molecular sieves, etc. It must be understood that this list of catalysts is only exemplary, and is not restrictive to the invention.

Preferably, the catalysts are solid under normal conditions. However, when the isomerization reaction temperature exceeds the catalyst's melting point, the catalyst is used in its molten state.

The preferred catalysts include inorganic salts such as hydrosulfates, pyrosulfates, hydrophosphates, perchlorates and similar salts, for example $KHSO_4$, $NaHSO_4$, $LiHSO_4$, $K_2S_2O_7$, $KH_2PO_4$, $NaH_2PO_4$, $K_2HPO_4$, $Na_2HPO_4$, $LiClO_4$, $NaHF_2$, etc.

The more preferred catalysts include hydrosulfates $KHSO_4$ and $NaHSO_4$. To the best of our knowledge, this is the first application of these hydrosulfates for the catalysis of the double bond migration; see for example R. Larock. Comprehensive Organic Transformations. VCH Publishers, Inc. 1989, Section "Isomerization of alkenes" (pp. 110–114).

The catalysts can be used in either anhydrous, or fused form or hydrated form, for example $NaHSO_4 \cdot H_2O$. The catalysts can be mixtures of two or more catalysts, or mixtures of active catalysts with catalytically inactive materials, or mixtures of the active catalysts with materials possessing lower catalytic activity.

Alternatively, the catalyst for use in the invention can be prepared by applying a catalytically active material onto the surface or into the volume of an inactive or less active material or sorbent, which is preferably solid at room temperatures. Still another alternative involves impregnating an inactive or less active material with a solution of a catalyst, with following optional removal of the solvent, which is usually water. An example of such modification is the $KHSO_4$/alumina catalyst.

Typically, the most preferred isomerization catalysts are those which provide for maximum isomerization of ketone 2 into ketones 4 and 19 and minimum cyclization of ketones 2, 19, and 4 into ketones 1, 3, 7, 8. Formation of significant amounts of ketone 1 during isomerization is rather undesirable because of its tendency to the secondary isomerization into 9.

A temperature range for the isomerization reaction is between about 0° C. and about 550° C. A preferred temperature range is between about 120° C. and about 300° C. The reaction can be carried out in the presence or in the absence of an organic solvent. Examples of suitable solvents include high boiling hydrocarbons such as heptadecane, high boiling point alcohols such as cetyl alcohol, glycols and the like.

The isomerization can be implemented in either batch or continuous format. It can be carried out under atmospheric pressure, under reduced pressure, or under increased pressure. For example, where the reaction is performed under conditions of continuous removal of ketone 4 by techniques such as fractional distillation, reduced pressures can be used. Alternatively, where the temperature is significantly higher than the boiling point of the ketones 2 and 4, the process can be performed in a sealed environment or under increased pressures.

During the reaction, starting ketone 2 can be in the liquid phase or in the vapor phase, or distributed between liquid and vapor phases. Ketone 4 boils at slightly lower temperature than ketone 2, therefore ketone 4, or a product enriched in ketone 4, can be continuously removed from the reaction mixture by fractional distillation.

A preferred weight ratio of ketone 2 to the catalyst in a batch process is between 0.1 to 500, and a more preferred weight ratio of ketone 2 to the catalyst is from about 0.5 to about 5. For continuous isomerization reactions, the weight ratio of ketone 2 to the catalyst is not limited.

Subsequent to isomerization, the isomerization product is subjected to the cyclization reaction. Quite surprisingly, in the cyclization of the isomerization product according to the invention, ketone 1 can be present in an improved yield, preferably, about 11% or higher, more preferably about 16% and higher. Thus, the ketone 1 can be considered a major product as opposed to a "minor impurity."

Under preferred conditions, the resulting concentration of ketone 1 can even exceed the concentration of any other cyclization product (ketones 3, 7, 8, 9); see, e.g., Example 7. This is even more surprising because it means that the cyclization of ketone 4 into ketone 1 (γ-isomer) is faster than the cyclization of 4 into ketone 9 (thermodynamically preferred β-isomer), faster than cyclization of 2 into 3, and also faster than the secondary isomerization of ketone 1 into 9 and other secondary isomerizations.

The cyclization process can be carried out over a wide variety of reaction conditions and in the presence or in the absence of organic solvents, in the presence or in the absence of hydroxyl-containing additives. Examples of solvents include high boiling hydrocarbons such as heptadecane, high boiling point alcohols such as cetyl alcohol, glycols and the like with examples of additive including alcohols and carboxylic acids such as those described in copending U.S. patent application Ser. No. 09/136,488, which is incorporated by reference in its entirety.

The cyclization can be performed either continuously or batch-wise. A preferred temperature range for the cyclization is from about 0° C. to about +150° C. Moreover, this step is preferably performed in the presence of cyclization catalyst. In this regard, acid catalysts are preferred.

The process of the cyclization can be carried out with a great variety of acid catalysts or mixtures of acid catalysts, including any catalyst known in the art for cyclizing 1,5-dienes. The acid catalyst for the cyclization can be any Lewis or Brönsted acid. Typically, the acid catalyst is a Brönsted acid, a mixture of Brönsted acids, or a solution of one or more Brönsted acids in water. Preferred Brönsted acids are either organic or inorganic and include phosphoric, sulfuric, formic, p-toluenesulfonic, and sulfosalicylic acids. Most preferred acid catalysts are phosphoric, sulfuric, and formic acids, and their solutions in water.

The cyclization is carried out with a preferred weight ratio of the intermediate isomeric mixture to the acid catalyst from about 0.1 to about 100. A more preferred weight ratio of the isomeric mixture to the acid catalyst is from about 0.5 to about 10.

When the cyclization is carried out in the presence of aqueous acids, formation of some small amounts of by-product hydroxyketones 21 and 22 may be observed (Scheme 6), which can be readily separated from the main product by distillation.

Scheme 4

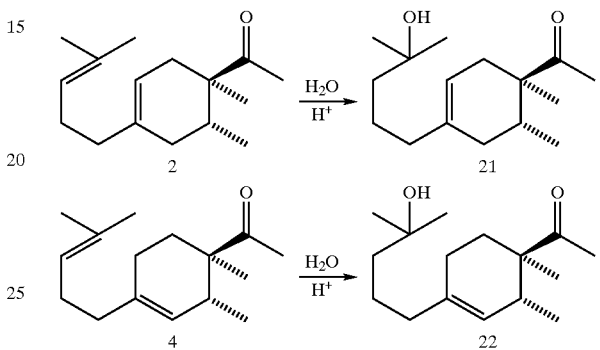

The higher boiling fraction containing hydroxyketones 21 and 22 can be cyclized separately to give additional quantities of the cyclization product having a similar isomeric composition, usually with slightly lower levels of ketone 1.

After the cyclization step, a product containing ketone 1, preferably as one of the major components or as the major component, can be used as a fragrance or a component of a fragrance without additional purification. Alternatively, ketone 1 can be isolated and purified by conventional means, such as:
  fractional distillation;
  crystallization of impurities at reduced temperature;
  oximation with hydroxylamine followed by crystallization and recrystallization of the oxime, then followed by regeneration from the oxime; or
  any combination of these methods.

After the cyclization, separation of the catalyst from the isomerization product is not necessary, but is preferred, especially in the case when it is desirable to reuse the catalyst in the next isomerization reaction. Optionally, the product of the isomerization reaction can be distilled (fast "rush-over" distillation) before the cyclization. Another option is a fractional distillation of the isomerization product in order to obtain fractions containing a higher concentration of ketone 4 before the cyclization. By-product fractions containing lower concentrations of ketone 4 can be reused (after optional redistillation) in the isomerization reaction.

Isolation and purification of ketone 1 from mixtures containing it in increased concentration, e.g., 12% and higher, is significantly easier than its isolation from mixtures containing less than 10%. It must be noted also that practically all concomitant materials obtained in the course of such purification process—mixtures containing mostly isomers 1, 3, 7, 8, 9—are themselves usable as aroma chemicals.

Thus, the invention provides a convenient environmentally benign and highly practical two-step process for obtaining ketone 1. The process provides higher yields of the target material as compared to the known methods.

The advantages of the invention will be realized and attained by means of the elements and combinations particularly pointed out in the claims. It is to be understood that both the foregoing description of the invention and the following examples are exemplary and explanatory only and are not restrictive of the invention, as claimed.

EXAMPLES

Example 1

Isomerization of Ketone 2 in the Presence of Crystalline Potassium Hydrogensulfate $KHSO_4$ Run 1a. A mixture of 1320.6 g of 92–94% purity ketone 2 and 465.8 g of crystalline potassium hydrogensulfate (Aldrich Catalog, No 22,347-6) was stirred 2 hours at about 195° C., cooled and filtered to give 1296.1 g of a filtrate and 472.2 g of recovered potassium hydrosulfate catalyst. The filtrate contained (GC): ketone 2, 47.2%; ketone 3, 4.1%; ketone 4, 28.0%; ketone 7, 1.4%; ketone 8, about 3%; ketones 19 and 20, about 8%.

Run 1b. The process was carried out in the same fashion as in Run 1a using 1321.8 g of ketone 2 and 466.5 g of the recovered catalyst. Weight of filtrate obtained: 1314.7 g, weight of recovered catalyst: 459.4 g. The filtrate contained (GC): ketone 2, 47.6%; ketone 3, 3.2%; ketone 4, 28.2%; ketone 7, 1.3%; ketone 8, about 3%; ketones 19 and 20, about 8%.

Run 1c The process was carried out in the same fashion as in Runs 1a and 1b using 1324.6 g of ketone 2 and 461.2 g of the catalyst recovered from Run 1b. Weight of filtrate obtained: 1316.4 g, weight of recovered catalyst: 457.8 g. The filtrate contained (GC): ketone 2, 47.7%; ketone 3, 3.2%; ketone 4, 28.2%; ketone 7, 1.3%; ketone 8, about 3%; ketones 19 and 20, about 8%. Total amount of 92–94% purity ketone 2 used in Runs 1a–1c was 3967.0 g. Filtrates obtained in all three runs (1a,b,c) were combined (3942.5 g) and used in the following cyclization reactions (Example 2).

Example 2

Cyclization of Undistilled Isomerization Product

Run 2a. A mixture of 1002.0 g of undistilled combined filtrate obtained in Example 1 and 506 g of 85% aqueous phosphoric acid was stirred at 30–36° C. over a period of 35 hours, then diluted with about 400 ml of heptane and 400 ml of water and stirred for another hour. After separation of the layers, the organic layer was washed with 30% aqueous NaOH, with water, the heptane was evaporated and the product was distilled to give 868.1 g (86.6% weight yield) of an isomeric mixture containing enhanced quantities of ketone 1, and also 94.2 g (about 9% theory yield) of a higher boiling fraction containing predominantly hydroxyketones 21 and 22. Total yield 95.5%. The reaction was repeated 3 more times (Runs 2b, 2c, 2d), and the distilled products obtained were blended together. The results are given in Tables E2-1 and E2-2.

TABLE E2-1

Yields of cyclization products.

| Run # | Filtrate used, g | Distilled cyclization product, g | Weight yield of distilled cyclization product, % | Fraction of hydroxy-ketones, g | Theory yield of hydroxy-ketones, % | Total theory yield, % |
|---|---|---|---|---|---|---|
| 2a | 1002.0 | 868.1 | 86.6 | 94.2 | 8.8 | 95.5 |
| 2b | 1005.8 | 891.4 | 88.6 | 65.0 | 6.0 | 94.6 |
| 2c | 1004.2 | 906.6 | 90.3 | 50.7 | 4.7 | 95.0 |
| 2d | 906.3 | 792.8 | 87.5 | 49.4 | 5.1 | 92.6 |
| Total | 3918.3 | 3458.9 | 88.3 | 259.3 | 6.15 | 94.45 |

TABLE E2-2

Composition of cyclization products (only major components given).

| | Composition, % (GC): | | | | |
|---|---|---|---|---|---|
| Run | Ketone 1 | Ketone 3 | Ketone 7 | Ketone 8 | Ketone 9 |
| 2a | 17.3 | 23.1 | 17.9 | 11.1 | 5.8 |
| 2b | 17.2 | 23.7 | 17.3 | 11.3 | 5.5 |
| 2c | 16.8 | 22.9 | 17.4 | 11.0 | 5.4 |
| 2d | 17.1 | 23.7 | 17.3 | 11.3 | 5.6 |
| Blend | 17.1 | 23.5 | 17.5 | 11.2 | 5.6 |

Theoretical yield of ketone 1 through Examples 1 and 2 is 16.0–16.4% based on starting ketone 2.

Example 3

Isomerization of Ketone 2 in the Presence of Potassium Hydrogensulfate with Following Fast Distillation of the Reaction Product Three isomerization reactions were carried out as in Example 1, but in each case the filtrate was fast distilled ("stripped"). Totally 3803.9 g of ~92% purity ketone 2 was used, and 3566.9 g (yield 93.8%) of distilled isomerization product was obtained. Composition (GC): ketone 2, 46.8%; ketone 3, 4.4%; ketone 4, 28.7%; ketone 7, 1.6%; ketone 8, about 3%; ketones 19 and 20, about 7%. The product was used in the following cyclization reactions (Example 4).

Example 4

Cyclization of Fast-distilled Isomerization Product

Four cyclization reactions (runs 4a, 4b, 4c, 4d) were carried out similarly to the Example 2, but at slightly different temperatures and reaction times. After the distillation, the products obtained were blended together. The results are given in Tables E4-1 and E4-2.

TABLE E4-1

Yields of cyclization products.

| Run # | Temp., °C./ reaction time, h | Product of example 3 taken into reaction, g | Distilled cyclization product, g | Yield of distilled cyclization product, % | Fraction of hydroxy-ketones, g | Theory yield of hydroxy-ketones, % | Total theory yield, % |
|---|---|---|---|---|---|---|---|
| 4a | 37–38/24 | 960.0 | 936.0 | 97.5 | — | — | 97.5 |
| 4b | 35–36/26 | 960.0 | 888.3 | 92.5 | 66.3 | 6.4 | 98.9 |
| 4c | 25–31/58 | 1006.0 | 949.6 | 94.4 | 16.6 | 1.5 | 95.9 |
| 4d | 30–40/39 | 615.1 | 551.7 | 89.7 | 32.6 | 4.9 | 94.6 |
| Total | | 3541.1 | 3325.6 | 93.9 | 115.5 | 3.0 | 96.9 |

TABLE E4-2

Composition of cyclization products (only major components given).

| | Composition, % (GC): | | | | |
|---|---|---|---|---|---|
| Run | Ketone 1 | Ketone 3 | Ketone 7 | Ketone 8 | Ketone 9 |
| 4a | 13.6 | 29.9 | 17.7 | 11.2 | 9.2 |
| 4b | 17.2 | 24.9 | 17.3 | 11.3 | 5.7 |
| 4c | 15.9 | 24.8 | 19.8 | 11.3 | 7.5 |
| 4d | 17.0 | 23.8 | 17.7 | 11.2 | 5.4 |
| Blend | 15.8 | 26.2 | 18.2 | 11.3 | 7.2 |

Theoretical yield of ketone 1 through Examples 3 and 4 is 15% based on starting ketone 2.

Example 5

Isomerization of Ketone 2 in the Presence of Potassium Hydrogensulfate with Following Column Distillation of the Reaction Product Three isomerization reactions were carried out as in Example 4. Totally 3902.7 g of 92% purity ketone 2 was used, and 3682.4 g (weight yield 96.8%) of fast-distilled isomerization product was obtained. Composition (GC): ketone 2, 47.0%; ketone 3, 4.9%; ketone 4, 28.7%; ketone 7, 2.0%; ketone 8, about 2%; ketones 19 and 20, about 7%. The product was redistilled at 3 mm Hg and reflux ratio 40:10, on a 5'×2"glass column filled with standard stainless steel protrusion packing. The redistillation afforded:

5-1) 443.4 g of "light" fractions (code 5-1) containing: ketone 1, 1.7%; ketone 2, 12.4%, ketone 3, 27.6%; ketone 4, 13.1%; ketone 7, 7.4%; ketones 8, 19, and 20, 1.7%; ketone 9, 11.8%.

5-2) 916.3 g of combined intermediate fractions (code 5-2) containing: ketone 2, 45.7%, ketone 3, 5.4%; ketone 4, 34.3%; ketone 7, 2.6%; ketones 8, 19, and 20, 5.5%;

5-3) 2209.5 g of material ("heart" cut code 5-3) containing: ketone 2, 49.0%; ketone 3, 1.2%; ketone 4, 39.9%; ketone 7, 0.8%; ketones 8, 19 and 20, 5.6%;

The combined intermediate fractions (code 5-2) were redistilled on the same column to give:

5-2a) 437.4 g of material 5-2a containing: ketone 2, 48.05%; ketone 3, 2.0%; ketone 4, 42.1%; ketone 7, 1.6%; ketones 8, 19 and 20, 4.0%;

5-2b) 165.4 g of material 5-2b containing: ketone 2, 59.8%; ketone 4, 32.5%; ketones 8, 19 and 20, 7.3%;

5-2c) 250.3 g of material 5-2c containing less than 30% of ketone 4.

Example 6

Cyclization of the "Heart" Fraction 5-3

The "heart" fraction 5-3 obtained in Example 5 was subjected to the cyclization conditions and work-up similar to those given in the Example 4. The cyclization afforded:

6-1) 1992.3 g of cyclization product 6-1 containing: ketone 1, 20.5%; unreacted ketone 2, 3.25%; ketone 3, 21.6%; unreacted ketone 4, 2.5%; ketone 7, 17.1%; ketone 8, 11.1%; ketone 9, 6.7%;

6-2) 70.1 g of a higher boiling fraction 6-2 containing predominantly hydroxyketones 21 and 22.

Example 7

Cyclization of material 5-2a

Material 5-2a obtained in Example 5 was subjected to the cyclization conditions and work-up similar to those given in the Example 4. The cyclization afforded:

7-1) 366.4 g of cyclization product 7-1 containing: ketone 1, 21.9%; unreacted ketone 2, 3.8%; ketone 3, 20.8%; unreacted ketone 4, 2.8%; ketone 7, 17.4%; ketone 8, 10.9%; ketone 9, 6.6%;

7-2) 15.4 g of a higher boiling fraction 7-2 containing predominantly hydroxyketones 21 and 22.

Example 8

Cyclization of Material 5-2b

Material 5-2b obtained in Example 5 was subjected to the cyclization conditions and work-up similar to those given in the Example 4. The cyclization afforded 127.2 g of cyclization product 8-1 containing: ketone 1, 18.6%; unreacted ketone 2, 6.8%; ketone 3, 20.2%; unreacted ketone 4, 4.4%; ketone 7, 18.4%; ketone 8, 12.2%; ketone 9, 5.3%.

Example 9

Cyclization of Hydroxyketones 21 and 22

Higher boiling fractions 6-2 and 7-2 obtained in Examples 6 and 7 were combined. The resulting mixture (85.5 g) containing 38.8% of hydroxyketone 21 and 23.6% of hydroxyketone 22 was cyclized in the presence of 51.3 g of 85% phosphoric acid over a period of 8 hours at 27–34° C., then 22 hours at 40–58° C. The reaction mixture was worked-up as in example 2 and distilled to give 61.6 g of cyclization product 9-1 which contained: ketone 1, 12.4%;

unreacted ketone 2, 7.0%; ketone 3, 27.0%; unreacted ketone 4, 6.3%; ketone 7, 10.8%; ketone 8, 12.4%; ketone 9, 9.1%. yield of ketone 1 in Examples 5 through 9 is 14.9% based on ketone 2 contained starting material.

Example 10

Fractional Distillation of the Cyclization Product

A 3422.8-g portion of the cyclization product obtained in Example 2 (Table E-2, "blend") was redistilled at 3 mm Hg and reflux ratio 40:10, on a 5'×2" glass column filled with standard protruded metal packing (PRO-PAK; stainless steel). The redistillation gave 14 fractions whose weights and composition are given in Table 10.

TABLE E10

Fractional distillation of the cyclization product.

| Fraction # | Weight, g | Ketone 1 | Ketone 2 | Ketone 3 | Ketone 4 | Ketone 7 | Ketone 8 | Ketone 9 | Hydroxy ketones 21 & 22 |
|---|---|---|---|---|---|---|---|---|---|
| Starting blend | 3422.8 | 17.1 | 3.8 | 23.5 | 2.9 | 17.5 | 11.2 | 5.5 | 3.4 |
| 1 | 238.5 | 2.0 | — | 25.0 | — | 7.7 | 0.3 | 12.9 | — |
| 2 | 225.2 | 4.3 | — | 44.8 | — | 15.6 | 0.6 | 16.5 | — |
| 3 | 222.0 | 5.4 | 0.3 | 46.9 | 0.4 | 18.4 | 0.8 | 14.8 | — |
| 4 | 236.8 | 6.5 | 0.3 | 46.7 | 0.5 | 20.5 | 1.0 | 13.2 | — |
| 5 | 237.0 | 8.9 | 0.5 | 44.3 | 0.6 | 23.8 | 1.5 | 10.5 | — |
| 6 | 235.7 | 11.6 | 0.7 | 40.8 | 0.9 | 27.0 | 2.1 | 7.6 | — |
| 7 | 237.3 | 15.6 | 1.0 | 35.1 | 1.3 | 29.9 | 3.0 | 5.3 | — |
| 8 | 235.2 | 21.3 | 1.2 | 27.8 | 1.6 | 31.9 | 4.2 | 3.3 | — |
| 9 | 216.7 | 29.7 | 2.2 | 18.1 | 2.7 | 31.6 | 7.3 | 1.3 | — |
| 10 | 239.7 | 39.6 | 3.8 | 8.5 | 4.6 | 25.5 | 12.6 | 0.4 | — |
| 11 | 240.2 | 45.8 | 6.3 | 2.3 | 6.7 | 14.3 | 21.6 | — | — |
| 12 | 232.1 | 38.2 | 10.9 | 0.7 | 9.3 | 5.1 | 34.3 | — | — |
| 13 | 226.2 | 16.3 | 18.6 | — | 10.4 | 0.9 | 50.5 | — | — |
| 14 | 221.0 | 1.0 | 21.0 | — | 7.1 | — | 29.4 | — | — |
| Residue | 152.7 | — | 0.7 | — | 0.2 | — | 0.7 | — | 61.1 |

Σ 3396.3

Example 11

Synthesis of Oxime of Ketone 1

A 212.2-g portion of Fraction 11 from Example 10 was refluxed for 15.5 hours with excess of ethanolic solution of hydroxylamine, allowed to stay two days at room temperature, then diluted with about double volume of water. The crystalline precipitate formed was filtered off to give 81.8 g of 87.9% purity oxime of ketone 1 (yield 69.5% based on the content of ketone 1 in Fraction 11). Recrystallization from heptane gave 65.6 g of practically pure oxime of ketone 1 (yield 63.4% based on the content of ketone 1 in Fraction 11).

Example 12

Regeneration of Ketone 1 from its Oxime

A mixture of 600 g of acetone, 316 g of 12.7% aqueous sulfuric acid, and 30 g of the oxime obtained according to Example 11, was refluxed until conversion of the oxime into ketone 1 reached ~80% by GLC analysis (15 hours). The mixture was cooled to 5° C. and filtered from crystalline unreacted oxime. Acetone was evaporated under reduced pressure, the remaining mixture was extracted with heptane, the heptane extract was washed with water, with saturated $NaHCO_3$, filtered through a pad of $MgSO_4$, the heptane was evaporated, and the residue distilled in vacuum to give 20.1 g (yield 71.3%) of practically pure ketone 1, b.p. ~107° C. /1 mm Hg.

Example 13

Preparation of Catalyst from $KHSO_4$ and $SiO_2$

A mixture of 33 g of crystalline $KHSO_4$ (m.p. 197° C.) and 100 g of silica (Davison Chemicals, Grade 12, 28–200 mesh) was fused in the oven at 250° C. for 2 hours, with occasional stirring. The resulting powder was used as the isomerization catalyst in Example 25 (see Table E15–35).

Example 14

Preparation of Catalyst from $KHSO_4$ and Alumina

A mixture of 100 g of alumina (activated, weakly acidic, Brockmann I, ~150 mesh, 58 Å, surface area 155 $m^2/g$) and 93 g of saturated aqueous solution of $KHSO_4$ (33 g of $KHSO_4$ in 60 g of water) was heated in oven at 105–115° C. for ~4.5 hours, with occasional stirring. The resulting powder was used as the isomerization catalyst in Examples 27 and 28 (see Table E15–35).

Examples 15–35

Isomerization of Ketone 2 in the Presence of Various Catalysts

A mixture of ketone 2 and a catalyst was stirred at given temperature and periodically analyzed by GLC. Catalysts, reaction conditions, and results of analyses are given in Table E15–35.

TABLE E15-35

Examples 15–35. Note: ketones 8, 19, 20 practically co-elute in QLC, so their simultaneous quantitative determination is difficult.

| Ex. # | Catalyst and its amount (% of ketone 2 by weight) | Reaction time and temperature | Isomerization products, % by GLC | | | Major cyclization products, % by GLC | | | |
|---|---|---|---|---|---|---|---|---|---|
| | | | Ketone 2 (unreacted) | Ketone 4 | Ketones 19 + 20 | Ketone 3 | Ketone 7 | Ketone 8 | Ketones 9 and 1 |
| 1 | KHSO₄ crystalline (35) | 2 hours at 195° C. | 47.2 | 28.2 | ~8 | 4.1 | 1.4 | ~3 | 0.7 and 0.4 |
| 15 | KHSO₄ fused (40) | 2.3 hours at 160° C. | 43.3 | 24.3 | ~6 | 5.9 | 3.6 | ~4 | 1.2 and 1.2 |
| 16 | KHSO₄ fused (40) | 20 min at 190° C. | 48.4 | 23.9 | ~8 | 3.7 | 2.0 | ~3 | trace and 0.6 |
| 17 | KHSO₄ crystalline (40) | 8 hours at 160° C. | 46.0 | 26.1 | ~7 | 4.6 | 2.4 | ~3 | trace and 0.7 |
| 18 | NaHSO₄ (31) | 20 min at 195° C. | 20.8 | 13.8 | — | 28.9 | 3.4 | 5.8 | 10.7 and 1.4 |
| 19 | NaHSO₄ (31) | 25 min at 140° C. | 71.4 | 8.2 | ~13 | 0.9 | 0.8 | ~2 | — |
| | | 2 hours at 140° C. | 29.4 | 18.1 | ~1 | 18.8 | 7.2 | ~8 | 4.8 and 4.2 |
| 20 | NaHSO₄·H₂O (33) | Heating from 22° to 150° C. for 8 min | No reaction | | | | | | |
| | | Heating from 150 to 195° C. for 4 min | 58.1 | 17.1 | ~13 | 2.0 | 1.4 | ~2 | trace and 0.2 |
| | | 10 min at 195° C. | 31.4 | 20.1 | — | 17.6 | 3.6 | ~8 | 6.5 and 1.5 |
| | | 20 min at 195° C. | 23.8 | 15.6 | — | 26.0 | 3.5 | 6.5 | 10.0 and 1.5 |
| 21 | NaHSO₄·H₂O (33) | Heating from 24 to 165° C. for 20 min | 75.5 | 6.2 | ~13.5 | 0.4 | 0.4 | ~0.5 | — |
| | | 10 min at 165° C. | 53.1 | 19.4 | ~7 | 4.0 | 2.5 | ~5 | 0.4 and 0.7 |
| | | 20 min at 165° C. | 41.5 | 22.8 | ~4 | 8.8 | 4.1 | ~6.5 | 1.8 and 1.8 |
| | | 30 min at 165° C. | 35.8 | 21.7 | — | 13.1 | 4.9 | 9.4 | 2.4 |
| 22 | K₂SI₇ (66) | Heating from 24° to 100° C. for 30 min | 54.2 | 8.8 | ~7 | 10.8 | 4.6 | ~6 | 0.4 and 0.5 |
| | | 1 hour at 100° C. | 34.6 | 11.7 | ~2 | 21.4 | 8.5 | ~9.5 | 1.4 and 2.2 |
| 23 | K₂SO₇ (33) | 1.5 hours at 75° C. | 70.9 | 5.9 | ~8 | 4.2 | 2.2 | ~3 | 0.0 and 0.1 |
| | | +50 min at 85° C. | 62.9 | 7.5 | ~6 | 7.0 | 3.8 | ~6 | trace and 0.4 |
| 24 | Silica (Davison, grade 12, 28–200 mesh) (33) | Heating from 24 to 150° C. for 15 min | No reaction | | | | | | |
| | | Heating from 150 to 195° C. for 11 min | 80.4 | 5.7 | ~5 | 2.2 | 0.8 | ~3 | — |
| | | 40 min at 195° C. | 55.0 | 9.2 | ~5 | 10.2 | 2.7 | ~11 | 0.6 and 0.3 |
| | | 130 min at 195° C. | 34.6 | 11.9 | — | 21.5 | 5.0 | ~13 | 1.9 and 0.8 |
| 25 | KHSO₄/silica catalyst prepared | Heating from 24° to 195° C. | 51.2 | 7.3 | ~1 | 17.1 | 3.1 | ~11.5 | 1.7 and 0.5 |

TABLE E15-35-continued

Examples 15–35. Note: ketones 8, 19, 20 practically co-elute in QLC, so their simultaneous quantitative determination is difficult.

| Ex. # | Catalyst and its amount (% of ketone 2 by weight) | Reaction time and temperature | Isomerization products, % by GLC | | | Major cyclization products, % by GLC | | | |
|---|---|---|---|---|---|---|---|---|---|
| | | | Ketone 2 (unreacted) | Ketone 4 | Ketones 19 + 20 | Ketone 3 | Ketone 7 | Ketone 8 | Ketones 9 and 1 |
| | according to Example 13 (33) | for 20 min 10 min at 195° C. | 22.5 | 8.3 | — | 37.5 | 5.2 | ~9 | 4.6 and 1.0 |
| 26 | Al$_2$O$_3$ activated, weakly acidic Brockman I (33) | 1.5 hours at 195° C. +30 min at 220° C. | No reaction No reaction | | | | | | |
| 27 | KHSO$_4$/alumina catalyst prepared according to Example 14 (33) | 6.3 hours at 195° C. +90 min at 220° | 68.5 59.8 | 8.1 12.0 | ~16 ~14 | 1.2 2.5 | 1.5 2.7 | ~1.5 ~3.5 | — trace and 0.2 |
| 28 | KHSO$_4$/alumina catalyst prepared according to Example 14 (33) | 2 hours at 220° C. 5.5 hours at 220° C. | 54.2 38.0 | 14.2 18.9 | ~10 ~3 | 4.4 10.6 | 3.4 6.4 | ~6 ~10 | 0.3 and 0.4 1.3 and 1.7 |
| 29 | Acidic clay (Engelhard XJ-9118) | 10 hours at 70° C. | 26.6 | 7.9 | — | 31.0 | 8.7 | ~11 | ~3.0 and 2.0 |
| 30 | Zeolite CBV-400 (Zeolyst International) 35 | Heating from 24° to 160° C. for 45 min Heating from 160 to 195° C. for 25 min | 69.3 7.8 | 8.1 6.0 | ~4 — | 6.1 41.5 | 1.7 8.1 | ~6 ~10 | 0.3 and 0.0 7.8 and 2.0 |
| 31 | K$_2$SO$_4$ (45) | 4 hours at 195° C. | No reaction | | | | | | |
| 32 | H$_3$BO$_3$ (16) | 2 hours at 195° C. | 72.6 | 6.6 | ~11 | 2.5 | 0.6 | ~3 | 0.2 and 0.0 |
| 33 | LiClO$_4$ (0.44) and oxalic acid dihydrate (0.88); 35% solution of ketone 2 in toluene | 30 min at 80° C. 50 min at 80° C. ~2 hours at 80° C. | 41.1 26.7 7.6 | 12.4 12.0 5.1 | ~4 ~2 — | 14.7 22.6 42.4 | 8.6 12.0 15.1 | ~10 ~10 6.5 | — and 1.8 1.5 and 4.1 5.8 and 7.8 |
| 34 | Silcotungstic acid hydrate (0.22) | 30 min at 90° C. | 38.6 | 8.4 | ~4 | 20.2 | 8.0 | ~8.5 | trace and 1.1 |
| 35 | KOH (33) | 2 hours at 195° C. | No reaction | | | | | | |

What is claimed is:

1. A process for obtaining ketone of formula 1a,b in its racemic or optically active form, comprising;

(a) contacting a ketone represented by formula 2a,b in its optically active or racemic form with a first catalyst under conditions and for a time sufficient to obtain an intermediate mixture, which intermediate mixture contains a ketone represented by formula 4a,b in its optically active or racemic form; and (b) contacting the intermediate mixture, or a fraction thereof, with a second catalyst under conditions effective to provide a product containing a ketone formula 1a,b, wherein the first catalyst differs from the second catalyst.

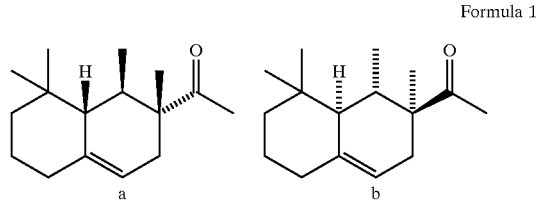

Formula 1

-continued

Formula 2
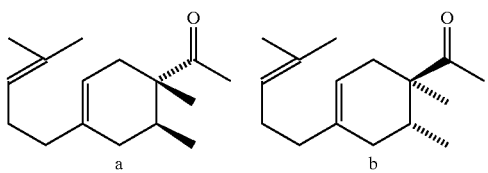

Formula 4
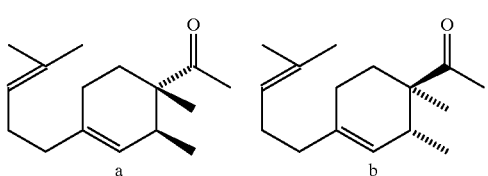

2. The process according to claim 1 wherein the first catalyst is an isomerization catalyst and the second catalyst is a cyclization catalyst.

3. The process of claim 1 wherein the conversion of ketone 2a,b to ketone 4a,b in step (a) is greater than about 11%.

4. The process of claim 1 wherein the conversion of ketone 2a,b to ketone 4a,b in step (a) is greater than about 20%.

5. The process of claim 1 wherein, in a process consisting essentially of steps (a) and (b), the conversion of ketone 2a,b to ketone 1a,b is greater than about 12%.

6. The process of claim 1 wherein the intermediate mixture further comprises ketones represented by formulas 20a,b and/or 19a,b.

Formula 20

Formula 19

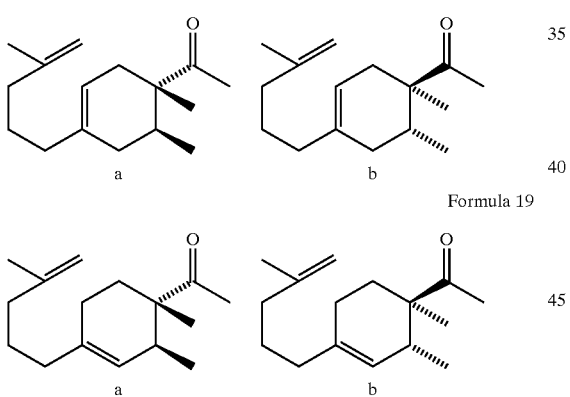

7. The process of claim 1 wherein the first catalyst comprises one or more salts selected from KHSO$_4$, NaHSO$_4$, K$_2$S$_2$O$_7$, LiHSO$_4$, KH$_2$PO$_4$, NaH$_2$PO$_4$, K$_2$HPO$_4$, Na$_2$HPO$_4$, NaHF$_2$, and LiClO$_4$.

8. The process of claim 1 wherein the first catalyst is prepared by applying a catalytically active material onto the surface or into the volume of an inactive or less active material or sorbent.

9. The process of claim 1 wherein the weight ratio of ketone 2a,b to the first catalyst is from about 0.1 to about 500.

10. The process of claim 1 wherein the weight ratio of ketone 2a,b to the first catalyst is from about 0.5 to about 5.

11. The process of claim 1 wherein the starting composition is contacted with the first catalyst at a temperature from about 0° C. to about 550° C.

12. The process of claim 1 wherein the starting composition is contacted with the first catalyst at a temperature from about 120° C. to about 300° C.

13. The process of claim 1 wherein step (a) is performed in a continuous operation.

14. The process of claim 1 wherein step (a) is performed in a batch operation.

15. The process of claim 1 further comprising, between steps (a) and (b), distilling the intermediate mixture, to obtain a first fraction enriched in ketone 4a,b and a second fraction enriched in ketone 2a,b, and wherein the first fraction is used in step (b).

16. The process of claim 15, wherein the second fraction is recycled into step (a) after optional redistillation.

17. The process of claim 1 wherein the cyclization catalyst of step (b) is aqueous or anhydrous phosphoric acid, sulfuric acid, formic acid, or a mixture thereof.

18. The process of claim 1 wherein step (b) is carried out at a temperature from about 0° C. to about +150° C.

19. The process of claim 1 further comprising, after step (b), separating ketone 1a,b from the rest of the product of step (b).

20. The process of claim 19 wherein ketone 1a,b is separated from the product of step (b) by at least one of: fractional distillation, oximation and hydrolysis of the oxime, and crystallization.

21. A process for obtaining ketone of formula 1a,b in its racemic or optically active form, comprising:
(a) contacting a ketone represented by formula 2a,b in its optically active or racemic form with a first catalyst under conditions and for a time sufficient to obtain an intermediate mixture, which intermediate mixture contains a significant quantity of ketone represented by formula 4a,b in its optically active or racemic form; and
(b) contacting the intermediate mixture, or a fraction thereof, with a second catalyst under conditions effective to provide a product containing a ketone of formula 1a,b, wherein the first catalyst differs from the second catalyst.

Formula 1
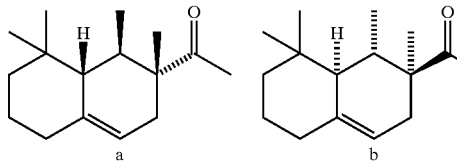

Formula 2
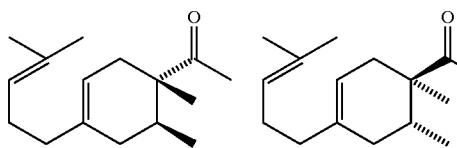

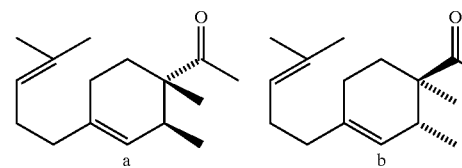

22. The process according to claim 21 wherein the amount of ketone 4a,b is not less than 11% by weight of the intermediate mixture.

23. The process according to claim 21 wherein the amount of ketone 4a,b is not less than 20% by weight of the intermediate mixture.

24. A process for obtaining ketone of formula 4a,b in its racemic or optically active form, comprising:

(a) providing a ketone represented by formula 2a,b in its optically active or racemic form; and (b) contacting the ketone of formula 2a,b with an isomerization catalyst under conditions and for a time sufficient to obtain a mixture, which mixture contains a significant quantity of ketone represented by formula 4a,b in its optically active or racemic form, and wherein the isomerization catalyst has a solid form under normal conditions.

25. A process for obtaining ketone of formula 1a,b in its racemic or optically active form, comprising:

(a) providing a mixture containing a ketone represented by formula 4a,b in its optically active or racemic form, wherein the mixture is produced by the process of claim 24; and (b) contacting the intermediate mixture, or a fraction thereof, with a cyclization catalyst under conditions effective to provide a product containing a ketone of formula 1a,b.

Formula 1

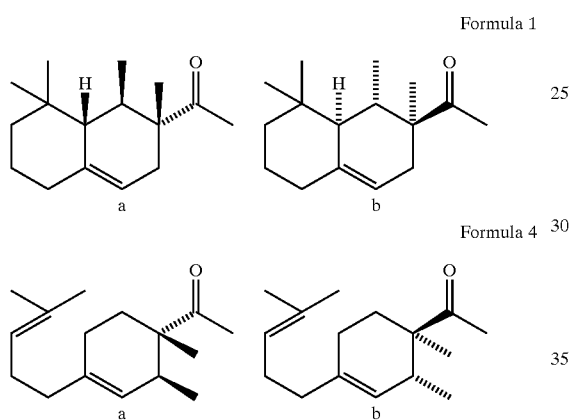

Formula 4

26. A process for obtaining ketone of formula 1a,b in its racemic or optically active form, comprising:

(a) contacting a ketone represented by formula 2a,b in its optically active or racemic form with a first catalyst under conditions and for a time sufficient to obtain an intermediate mixture, which intermediate mixture contains a ketone represented by formula 4a,b in its optically active or racemic form, wherein the first catalyst has a solid form under normal conditions; and (b) contacting the intermediate mixture, or a fraction thereof, with a second catalyst under conditions effective to provide a product containing a ketone of formula 1a,b, wherein the first catalyst differs from the second catalyst.

Formula 1

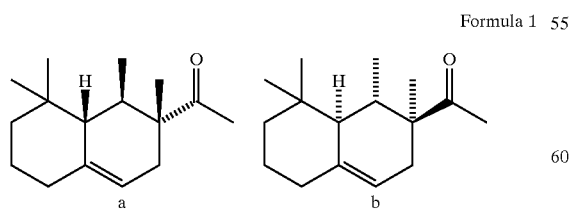

-continued

Formula 2

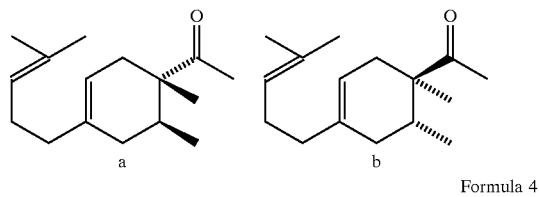

Formula 4

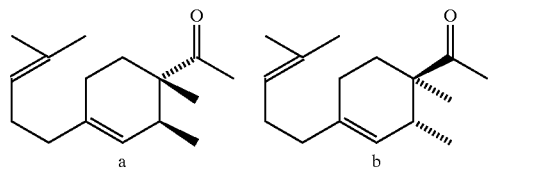

27. A process for obtaining ketone of formula 1a,b in its racemic or optically active form, comprising:

(a) contacting a ketone represented by formula 2a,b in its optically active or racemic form with a first catalyst under conditions and for a time sufficient to obtain an intermediate mixture, which intermediate mixture contains a significant quantity of ketone represented by formula 4a,b in its optically active or racemic form, wherein the first catalyst has a solid form under normal conditions; and (b) contacting the intermediate mixture, or a fraction thereof, with a second catalyst under conditions effective to provide a product containing a ketone of formula 1a,b, wherein the first catalyst differs from the second catalyst.

Formula 1

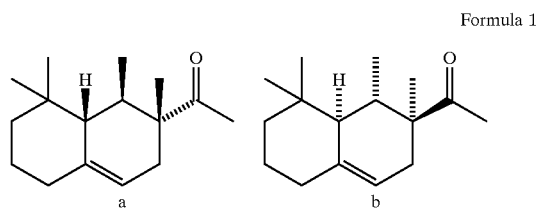

Formula 2

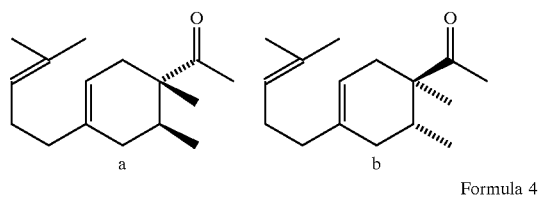

Formula 4

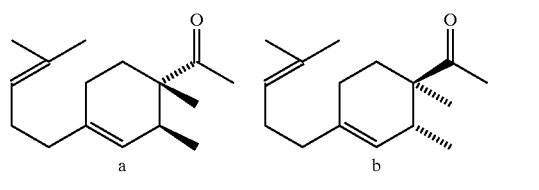

* * * * *